United States Patent
Kamohara

(12) 
(10) Patent No.: US 6,861,457 B2
(45) Date of Patent: Mar. 1, 2005

(54) DENTAL IMPRESSION MATERIAL COMPOSITION

(75) Inventor: Hiroshi Kamohara, Tokyo (JP)

(73) Assignee: GC Corporation, Tokyo (JP)

( * ) Notice: Subject to any disclaimer, the term of this patent is extended or adjusted under 35 U.S.C. 154(b) by 376 days.

(21) Appl. No.: 10/226,159

(22) Filed: Aug. 23, 2002

(65) Prior Publication Data

US 2003/0125411 A1 Jul. 3, 2003

(30) Foreign Application Priority Data

Sep. 5, 2001 (JP) ........................................ 2001-269306

(51) Int. Cl.$^7$ ................................................ A61K 6/10
(52) U.S. Cl. .......................... 523/109; 524/730; 528/31; 528/32
(58) Field of Search .......................... 523/109; 524/730; 528/31, 32

(56) References Cited

U.S. PATENT DOCUMENTS

| | | | |
|---|---|---|---|
| 5,637,628 A | | 6/1997 | Kamohara et al. |
| 5,849,812 A | | 12/1998 | Zech et al. |
| 5,907,002 A | * | 5/1999 | Kamohara et al. .......... 523/109 |

FOREIGN PATENT DOCUMENTS

| | | |
|---|---|---|
| GB | 2 337 524 | 11/1999 |
| WO | WO 96/32088 | 10/1996 |

OTHER PUBLICATIONS

Derwent Publications, JP 04–353564, Dec. 8, 1992.

\* cited by examiner

*Primary Examiner*—Tae H. Yoon
(74) *Attorney, Agent, or Firm*—Oblon, Spivak, McClelland, Maier & Neustadt, P.C.

(57) ABSTRACT

To provide a dental impression material composition having high hydrophilicity comparable to that of polyether rubber-made impression materials, being superior in recovery from deformation caused by removal out of an oral cavity, which are similar to silicone rubber-made impression materials, the dental impression material composition being superior in dimensional precision, and good in storage stability. The dental impression material composition includes (A) 100 parts by weight of the sum of (1) an organopolysiloxane containing at least two aliphatic unsaturated hydrocarbons in one molecule and (2) a polyether containing at least one aliphatic unsaturated hydrocarbon in one molecule, in a weight ratio of (1) to (2) of 1:0.01~1:5, having (B) 0.1~100 parts by weight of an organohydrogenpolysiloxane containing at least three hydrogen atoms directly bonded to a silicon atom in one molecule, (C) 10~500 ppm, based on the sum of (A) and (B), of a silicone-soluble platinum compound, (D) 10~800 parts by weight of an inorganic filler, and (E) 0.5~5 parts by weight of a nonionic surfactant and/or a polyether-modified silicone oil, compounded therewith.

1 Claim, No Drawings

DENTAL IMPRESSION MATERIAL COMPOSITION

BACKGROUND OF THE INVENTION

1. Field of the Invention

The present invention relates to a dental impression material composition to be used for taking an impression of an intra-oral shape for the purpose of preparation of dental prostheses such as a crown, an inlay, and a denture in the dental remedy. In particular, the present invention relates to a dental impression material composition that is superior in affinity with an intra-oral tissue, dimensional precision and storage stability.

2. Description of the Related Art

At present, impression materials made of various materials such as an alginate, agar-agar, silicone rubber, polysulfide rubber, and polyether rubber are used as a dental impression material. Of these, rubber-made impression materials made of silicone rubber, polysulfide rubber, or polyether rubber as a material, which are called rubber-made elastic impression materials, have superior dimensional precision and hence, are used where the precision is required. In particular, a silicone rubber-made impression material is a dental impression material that is most widely used among the rubber elastic impression materials. However, this silicone rubber-made impression material has very high water repellency intrinsic of its material per se. Accordingly, when the silicone rubber-made impression material is to be used for taking an intra-oral part where the water content such as saliva is very high, reproducibility of the details was poor and it is most likely to obtain an incomplete impression. For this reason, in order to improve this defect, silicone rubber-made impression materials comprising a silicone rubber-made impression material to which a surfactant, a polyether-modified silicone oil, etc. are added for the purpose of enhancing the hydrophilicity, are being broadly used. However, there were still involved problems that the hydrophilicity is not sufficient yet such that the reproducibility of the details is incomplete and that a defect likely to be partially generated in the taken impression due to an influence of the water content within the oral cavity.

As the rubber elastic impression material having high hydrophilicity is also known a polyether rubber-made impression material. This polyether rubber-made impression material is different from the silicone rubber-made impression material in that the material per se is a polymer containing a polyether having high hydrophilicity. Accordingly, there is less possibility that, thus not a few impressions become incomplete during the impression taking within an oral cavity. However, the polyether rubber-made impression material is poor in recovery from deformation applied during the time of taking-out from the oral cavity, as compared with the silicone rubber-made impression material. As a result, the polyether rubber-made impression material involved defects that it is deformed, leading to an inaccurate impression to cause a problem in dimensional precision and that it gives a patient an unpleasant feeling due to a peculiar odor and a bitter taste.

As an impression material composition having high hydrophilicity comparable to the polyether rubber-made impression material and having high dimensional precision comparable to the silicone rubber-made impression material, is proposed a curable composition comprising an alkenyl group-terminated polyether and an Si—H group-containing polyether, as disclosed in Japanese Patent Laid-open No. 293955/1992. However, this curable composition is poor in curing properties and storage stability so that it has not yet been put into actual use.

SUMMARY OF THE INVENTION

Thus, the present invention is aimed to provide a dental impression material composition that has high hydrophilicity comparable to currently employed polyether rubber-made impression materials, is superior in recovery from deformation applied during the time of taking-out from an oral cavity, similar to silicone rubber-made impression materials, is superior in dimensional precision, and is good in storage stability.

The present inventor made extensive and intensive investigations in order to achieve the above-described aim. As a result, it has been found that when to an organopolysiloxane containing at least two aliphatic unsaturated hydrocarbons in one molecule is added a polyether containing at least one aliphatic unsaturated hydrocarbon in one molecule in a specific proportion; an organohydrogenpolysiloxane containing at least three hydrogen atoms directly bonded to a silicon atom in one molecule as a crosslinking agent acting to both of the polyether and the organopolysiloxane is added to the mixture; a nonionic surfactant and/or a polyether-modified silicone oil is further added thereto for improving the affinity among the respective components, enhancing a reactivity as an impression material and preventing liquid separation; and a silicone-soluble platinum compound as a conventional addition type curing catalyst and an inorganic filler are compounded therewith, a dental impression material composition that has extremely high hydrophilicity, is superior in recovery from deformation, is superior in dimensional precision, and is good in storage stability can be obtained, leading to accomplishment of the present invention.

Specifically, the dental impression material composition according to the present invention is a dental impression material composition comprising (A) 100 parts by weight of the sum of (1) an organopolysiloxane containing at least two aliphatic unsaturated hydrocarbons in one molecule and (2) a polyether containing at least one aliphatic unsaturated hydrocarbon in one molecule, in a weight ratio of (1) to (2) of 1:0.01~1:5, having (B) 0.1~100 parts by weight of an organohydrogenpolysiloxane containing at least three hydrogen atoms directly bonded to a silicon atom in one molecule, (C) 10~500 ppm, based on the sum of (A) and (B), of a silicone-soluble platinum compound, (D) 10~800 parts by weight of an inorganic filler, and (E) 0.5~5 parts by weight of a nonionic surfactant and/or a polyether-modified silicone oil, compounded therewith.

DETAILED DESCRIPTION OF THE INVENTION

The organopolysiloxane (1) containing at least two aliphatic unsaturated hydrocarbons in one molecule in the component (A) of the dental impression material according to the present invention is preferably linear one, the both ends of which are terminated by a vinylsiloxy group. The vinylsiloxy group at the end may contain a plurality of vinyl groups or may contain a vinyl group or groups in a chain thereof. The polyether (2) containing at least one aliphatic unsaturated hydrocarbon in one molecule in the component (A) is a polyether containing a reactive aliphatic unsaturated hydrocarbon in the molecule thereof, similar to the organopolysiloxane (1), and preferably has a number average molecular weight of 200~15,000. Typical examples are specifically shown below.

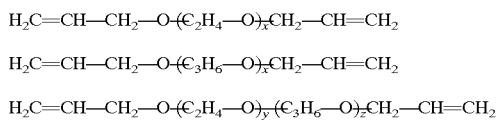

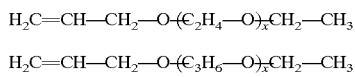

In the formulae, x is 3~300, and (y+z) is 3~300.

$H_2C=CH-CH_2-O-(C_2H_4-O)_x-CH_2-CH_3$ $H_2C=CH-CH_2-O-(C_3H_6-O)_x-CH_2-CH_3$

In the formulae, x is 3~300.

The compounds represented by the above formulae may be used either singly or in admixture of more than two thereof. The combination of the organopolysiloxane (1) and the polyether (2) can impart to the dental impression material composition high hydrophilicity as in the polyether rubber-made impression material as well as superiority in recovery from deformation as in the silicone rubber-made impression material. The characteristics of the dental impression material composition according to the present invention are obtained by the co-presence of the organopolysiloxane (1) and the polyether (2), and a suitable mixing ratio of the organopolysiloxane (1) to the polyether (2) is 1:0.01~1:5 on a weight basis. The high hydrophilicity of the dental impression material composition according to the present invention makes a characteristic caused by the polyether (2). Accordingly, in the case where the proportion of the organopolysiloxane (1) is "1", when the proportion of the polyether (2) is less than 0.01, sufficient hydrophilicity is not obtained, whereas when it exceeds 5, the recovery from deformation becomes worse. Incidentally, the dental impression material composition according to the present invention is generally supplied in a two components of a base paste and a catalyst paste. In this case, a mixing ratio of the organopolysiloxane (1) to the polyether (2) of the whole of the component (A) may be 1:0.01~1:5 on a weight basis. Further, it is desired from the standpoint of storage stability that the polyether (2) in the component (A) is not compounded in a catalyst paste to be contained in the component (C) as described later in detail.

The organohydrogenpolysiloxane as the component (B) contains at least three hydrogen atoms directly bonded to a silicon atom in the molecule thereof and acts as a crosslinking agent of the component (A). A suitable compounding amount of the component (B) is 0.1~100 parts by weight based on 100 parts by weight of the component (A). When the amount of the component (B) is less than 0.1 parts by weight, not only the hardness of the cured material is lowered, but also the curing rate becomes slow, whereas when it exceeds 100 parts by weight, the cured material becomes very brittle. In the case where the dental impression material composition according to the present invention is supplied in a two components of a base paste and a catalyst paste containing the component (C) as described later in detail, it is desired from the standpoint of storage stability that the component (B) is not compounded in the catalyst paste.

The silicone-soluble platinum compound as the component (C) acts as a catalyst for crosslinking polymerization of the component (A) and the component (B). Specific examples include chloroplatinic acid, alcohol-modified chloroplatinic acid, and a complex of chloroplatinic acid and an olefin, all of which are a known addition reaction catalyst. Of these is particularly preferred a vinylsiloxane complex of chloroplatinic acid. A suitable addition amount of the component (C) is in the range of 10~500 ppm based on the sum of the components (A) and (B). When the amount of the component (C) is less than 10 ppm, the curing rate is so slow that in the case where a trace amount of a substance retarding the catalytic function of the platinum compound is present the trouble arises that, the curing becomes slow. On the other hand, when it exceeds 500 ppm, the curing rate becomes too fast, suffering economical disadvantage. It is preferred that the silicone-soluble platinum compound such as chloroplatinic acid is used upon being dissolved in an alcoholic, ketone-based, ether-based or hydrocarbon-based solvent or a polysiloxane oil.

The inorganic filler as the component (D) is a component for improving the workability before the curing or the physical properties after the curing. Examples of the inorganic filler include quartz, cristobalite, diatomaceous earth, fused quartz, glass fibers, titanium dioxide, and fumed silica all being in powers. A suitable compounding amount of the inorganic filler is from 10 to 800 parts by weight based on 100 parts by weight of the component (A). When the amount of the inorganic filler as the component (E) is less than 10 parts by weight, the cured material becomes brittle, whereas when it exceeds 800 parts by weight, the viscosity of the dental impression material composition before the curing becomes too high so that the workability becomes worse. Hence, such is not suitable.

The nonionic surfactant and/or the polyether-modified silicone oil as the component (E) has effects for enhancing the affinity with the compounds in the component (A) and for facilitating the crosslinking reaction by the component (B). As the nonionic surfactant to be suitably used as the component (E) are nonionic surfactants in which an alkyl group as an oleophilic group is combined with a hydrophilic group. Suitable examples of the nonionic surfactant include polyoxyethylene alkyl ethers, polyoxyethylene polyoxypropylene alkyl ethers, polyoxyethylene alkylphenyl ethers, and the like, in which the addition molar number of ethylene oxide or propylene oxide is 1~30; ether type nonionic surfactants in which the alkyl group has 12~22 carbon atoms; sorbitan fatty acid esters, glycerin fatty acid esters, polyglycerin fatty acid esters, ethylene glycol fatty acid esters, polyethylene glycol fatty acid esters, propylene glycol fatty acid esters, pentaerythritol fatty acid esters, and the like, which are of a type of a partial ester between a polyhydric alcohol and a fatty acid having 12~22 carbon atoms; polyoxyethylene sorbitan fatty acid esters, polyoxyethylene sorbitol fatty acid esters, polyoxyethylene mannitan fatty acid esters, polyoxyethylene glycerin fatty acid esters, polyoxyethylene propylene glycol mono-fatty acid esters, etc., which are of an ether-ester type in which the addition molar number of ethylene oxide is 1~30, and the fatty acid has 12~22 carbon atoms; and polyoxyethylene castor oil, hydrogenated castor oil, polyoxyethylene lanolin derivatives, polyoxyethylene beewax derivatives, and the like, which are of a type of an ester with ethylene oxide having an addition molar number of 1~30.

The polyether-modified silicone oil is a compound comprising a polyorganosiloxane having, in a side chain thereof, a polyether such as polyoxyethylene and polyoxypropylene, and is represented by the following general formula:

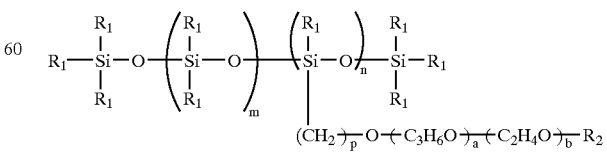

wherein $R_1$ is an alkyl group or an aryl group, each having from 1 to 15 carbon atoms; $R_2$ is a hydrogen atom or an alkyl group or an aryl group, each having 1~15 carbon atoms; n is a positive number of 5~100; m is a positive number of 1~100; p is a positive number of 0~10; a is a positive number of 0~50; and b is a positive number of 1~50.

These nonionic surfactants and/or the polyether-modified silicone oils may be used either singly or in admixture of more than two thereof. A suitable compounding amount of the component (E) is 0.5~5 parts by weight based on 100 parts by weight of the component (A). When the amount of the component (E) is less than 0.5 parts by weight, not only the affinity with the compounds as the component (A) becomes worse so that separation into two phases likely occurs, but the surface state after the curing becomes worse so that a sufficient performance as the dental impression material cannot be obtained. On the other hand, when it exceeds 5 parts by weight, the storage stability of the composition is lowered.

In addition, the dental impression material composition according to the present invention may as a matter of course be further compounded with various inorganic or organic coloring agents such as coloring agents used in usual silicone compositions, including red oxide, titanium white, titanium yellow, and cobalt blue, so far as the characteristics thereof are not hindered.

Next, the present invention will be described in detail with reference to the following Examples, but it should not be construed that the present invention is limited thereto.

EXAMPLE 1

A base paste and a catalyst paste, each having the following composition, were prepared.

| (Base paste) | |
|---|---|
| Component (A): (1) Dimethylpolysiloxane in which the both ends of the molecular chain are terminated by a dimethylvinylsiloxy group and (2) polyethylene glycol diallyl ether in which the both ends of the molecular chain are terminated by a vinyl group (a weight ratio of (1) to (2) = 1:0.05) | 100 g |
| Component (B): Linear methyl hydrogenpolysiloxane containing 45% by mole of a methyl hydrogensiloxane unit | 3 g |
| Component (D): Quartz powder | 10 g |
| Component (E): Polyoxyethylene alkyl ether | 1 g |
| (Catalyst paste) | |
| Component (A): (1) Dimethylpolysiloxane in which the both ends of the molecular chain are terminated by a dimethylvinylsiloxy group | 100 g |
| Component (C): Silicone oil solution containing 0.7% by weight of a 1,3-divinyltetramethyl disiloxane platinum complex | 3 g |
| Component (D): Quartz powder | 10 g |

Five grams of each of the base paste and the catalyst paste was weighed and kneaded. The kneaded mixture was built on a glass plate and pressed by another glass plate via a spacer from above, followed by curing to prepare a sample for contact angle measurement having a thickness of 2 mm and a diameter of 3 cm. Next, the contact angle of the sample, a contact angle was measured one second after adding dropwise a water droplet, using an automatic contact angle meter (a product name: CA-Z, manufactured by Kyowa Interface Science Co., Ltd.). Likewise, 5 g of each of the base paste and the catalyst paste was weighed and kneaded in the same manner as above. Then, recovery from deformation were measured in accordance with ISO 4823. For the storage stability, the base paste and the catalyst paste were filled in a tube made of aluminum, which was then stored at 60° C. for one week. Thereafter, recovery from deformation were measured in accordance with ISO 4823. The results obtained are summarized and shown in Table 1.

EXAMPLE 2

A base paste and a catalyst paste, each having the following composition, were prepared.

| (Base paste) | |
|---|---|
| Component (A): (1) Dimethylpolysiloxane in which the both ends of the molecular chain are terminated by a dimethylvinylsiloxy group, (2) polypropylene glycol diallyl ether in which the both ends of the molecular chain are terminated by a vinyl group, and (2) polyethylene glycol diallyl ether in which the both ends of the molecular chain are terminated by a vinyl group (a weight ratio of (1) to (2) to (2) = 1:0.3:0.2) | 100 g |
| Component (B): Linear methyl hydrogenpolysiloxane containing 45% by mole of a methyl hydrogensiloxane unit | 5 g |
| Component (D): Quartz powder | 200 g |
| Component (E): Polyoxyethylene alkyl ether | 2.0 g |
| (Catalyst paste) | |
| Component (A): (1) Dimethylpolysiloxane in which the both ends of the molecular chain are terminated by a dimethylvinylsiloxy group | 100 g |
| Component (C): Silicone oil solution containing 0.7% by weight of a 1,3-divinyltetramethyl disiloxane platinum complex | 5 g |
| Component (D): Quartz powder | 200 g |

The above-described pastes were subjected to the same tests as in Example 1. The results obtained are summarized and shown in Table 1.

EXAMPLE 3

A base paste and a catalyst paste, each having the following compositions, were prepared.

| (Base paste) | |
|---|---|
| Component (A): (1) Dimethylpolysiloxane in which the both ends of the molecular chain are terminated by a dimethylvinylsiloxy group and (2) polypropylene glycol diallyl ether in which the both ends of the molecular chain are terminated by a vinyl group (a weight ratio of (1) to (2) = 1:10) | 100 g |
| Component (B): Linear methyl hydrogenpolysiloxane containing 10% by mole of a methyl hydrogensiloxane unit | 150 g |
| Component (D): Quartz powder | 800 g |
| Component (E): Polyether-modified silicone oil (containing 10% by mole of polyoxyethylene) | 8.0 g |
| (Catalyst paste) | |
| Component (A): (1) Dimethylpolysiloxane in which the both ends of the molecular chain are terminated by a dimethylvinylsiloxy group | 100 g |
| Component (C): Silicone oil solution containing 0.7% by weight of a 1,3-divinyltetramethyl disiloxane platinum complex | 10 g |
| Component (D): Quartz powder | 800 g |

The above-described pastes were subjected to the same tests as in Example 1. The results obtained are summarized and shown in Table 1.

COMPARATIVE EXAMPLE 1

As a dental silicone rubber-made impression material having a composition similar to that of a conventional hydrophilic silicone rubber-made impression material, a base paste and a catalyst paste, each having the following compositions, were prepared.

| (Base paste) | |
|---|---|
| Dimethylpolysiloxane in which the both ends of the molecular chain are terminated by a dimethylvinylsiloxy group | 100 g |
| Linear methyl hydrogenpolysiloxane containing 40% by mole of a methyl hydrogensiloxane unit | 5 g |
| Polyoxyethylene alkyl ether | 10 g |
| Quartz powder | 200 g |
| (Catalyst paste) | |
| Dimethylpolysiloxane in which the both ends of the molecular chain are terminated by a dimethylvinylsiloxy group | 100 g |
| Silicone oil solution containing 0.4% by weight of a 1,3-divinyltetramethyl disiloxane platinum complex | 5 g |
| Quartz powder | 200 g |

Next, the base paste and the catalyst paste were subjected to the same tests as in Example 1. The results obtained are summarized and shown in Table 1.

COMPARATIVE EXAMPLE 2

Using a polyether rubber-made impression material (a product name: Impregum, made by ESPE Dental AG), the same tests as in Example 1 were carried out. The results obtained are summarized and shown in Table 1.

TABLE 1

| | Example No. | | | Comparative Example No. | |
|---|---|---|---|---|---|
| | 1 | 2 | 3 | 1 | 2 |
| Contact angle (degree) | 65 | 55 | 56 | 90 | 58 |
| Recovery from deformation (%) | 99.5 | 99.3 | 99.2 | 99.4 | 82.5 |
| Recovery from deformation after storing at 60° C. for one week (%) | 99.4 | 99.3 | 99.2 | 99.1 | 80.5 |

As is clear from Table 1, the dental impression material compositions of Examples 1 to 3 according to the present invention have a contact angle comparable to that of the currently employed polyether rubber-made impression material (Comparative Example 2), and hence, it can be understood that the dental impression material compositions of Examples 1 to 3 have superior hydrophilicity. Further, since the dental impression material compositions of Examples 1 to 3 according to the present invention have a high value for the recovery from the deformation comparable to that of Comparative Example 1 having a composition analogous to the conventional hydrophilic silicone rubber-made impression material, it can be confirmed that the dental impression material compositions of Examples 1 to 3 are superior in dimensional precision. Moreover, since the dental impression material compositions of Examples 1 to 3 according to the present invention have values for recovery from the deformation after storing at 60° C. for one week which are substantially equal to those before storing, the dental impression material compositions of Examples 1 to 3 can be confirmed as good in storage stability. On the other hand, though the silicone rubber-made impression material of Comparative Example 1, in which the hydrophilicity is enhanced using the conventional surfactant, has a high value for the recovery from deformation, it has a large contact angle and hence, is insufficient in hydrophilicity. Also, though the polyether rubber-made impression material of Comparative Example 2 has a small contact angle and hence, is high in hydrophilicity, it has a low value for the recovery from the deformation as compared with those of Examples 1 to 3 and Comparative Example 1, is inferior in dimensional precision, and is poor in storage stability.

As described above in detail, since the dental impression material composition according to the present invention has hydrophilicity comparable to that of currently employed polyether rubber-made impression materials, it is superior in affinity with an intra-oral tissue. Also, the dental impression material composition according to the present invention is high in recovery from deformation applied during the time of taking-out from an oral cavity, which are similar to silicone rubber-made impression materials, is superior in dimensional precision, and is good in storage stability. Accordingly, the present invention is greatly valuable in contributing to the dental remedy field.

While the present invention has been described in detail and with reference to specific embodiments thereof, it will be apparent to one skilled in the art that various changes and modifications can be made therein without departing from the spirit and scope thereof.

What is claimed is:

1. A dental impression material composition comprising:
    (A) 100 parts by weight of the sum of (1) an organopolysiloxane containing at least two aliphatic unsaturated hydrocarbons in one molecule and (2) a polyether containing at least one aliphatic unsaturated hydrocarbon in one molecule, in a weight ratio of (1) to (2) of 1:0.01~1:5,
    (B) 0.1~100 parts by weight of an organohydrogenpolysiloxane containing at least three hydrogen atoms directly bonded to a silicon atom in one molecule,
    (C) 10~500 ppm, based on the sum of (A) and (B), of a silicone-soluble platinum compound,
    (D) 10~800 parts by weight of an inorganic filler, and
    (E) 0.5~5 parts by weight of a nonionic surfactant and/or a polyether-modified silicone oil.

* * * * *